United States Patent
Manz et al.

(10) Patent No.: US 6,746,610 B2
(45) Date of Patent: Jun. 8, 2004

(54) OIL SYSTEM, IN PARTICULAR A HYDRAULIC OR LUBRICATING OIL SYSTEM

(75) Inventors: Rolf Manz, Öhringen (DE); Reinhard Wierling, Pfedelbach (DE)

(73) Assignee: Mahle Filtersysteme GmbH, Stuttgart (DE)

( * ) Notice: Subject to any disclaimer, the term of this patent is extended or adjusted under 35 U.S.C. 154(b) by 126 days.

(21) Appl. No.: 10/148,122

(22) PCT Filed: Nov. 29, 2000

(86) PCT No.: PCT/DE00/04234

§ 371 (c)(1),
(2), (4) Date: May 24, 2002

(87) PCT Pub. No.: WO01/40701

PCT Pub. Date: Jun. 7, 2001

(65) Prior Publication Data

US 2003/0116509 A1 Jun. 26, 2003

(30) Foreign Application Priority Data

Nov. 30, 1999 (DE) .......................................... 199 57 592

(51) Int. Cl.⁷ .......................... B01D 37/00; F16N 29/00; G01N 21/53
(52) U.S. Cl. ...................... 210/689; 210/745; 210/96.1; 210/168; 210/295; 210/416.5; 210/418; 210/DIG. 5; 73/53.05; 73/61.48; 356/70; 184/6.4
(58) Field of Search .................. 210/689, 745, 210/799, 96.1, 168, 295, 416.5, 418, DIG. 5; 73/53.05, 61.48, 61.61, DIG. 8; 356/70; 184/6.24, 6.4, 108

(56) References Cited

U.S. PATENT DOCUMENTS

| | | | | |
|---|---|---|---|---|
| 3,003,353 A | * | 10/1961 | Swadesh | 73/53.05 |
| 3,966,603 A | * | 6/1976 | Grant | 210/86 |
| 4,499,376 A | | 2/1985 | Frost et al. | |
| 4,609,458 A | * | 9/1986 | Okamura et al. | 210/85 |
| 4,649,281 A | * | 3/1987 | Schmitt et al. | 250/574 |
| 4,649,711 A | | 3/1987 | Sibley et al. | |
| 4,967,880 A | | 11/1990 | Krambs | |
| 5,049,742 A | | 9/1991 | Hosonuma et al. | |
| 5,599,460 A | | 2/1997 | Van Der Porten et al. | |
| 5,968,371 A | * | 10/1999 | Verdegan et al. | 210/739 |
| 6,478,953 B2 | * | 11/2002 | Spearman et al. | 210/130 |

FOREIGN PATENT DOCUMENTS

| | | |
|---|---|---|
| DE | 691 16 702 | 2/1991 |
| DE | 196 50 397 | 12/1996 |
| EP | 0 557 626 | 2/1992 |
| EP | 0 596 231 | 5/1994 |
| EP | 0 675 359 | 3/1995 |
| GB | 2 194 333 | 3/1988 |
| WO | 99 44043 | 9/1999 |
| WO | 99 58970 | 11/1999 |

* cited by examiner

Primary Examiner—Frank M. Lawrence
(74) Attorney, Agent, or Firm—Collard & Roe, P.C.

(57) ABSTRACT

The invention relates to an oil system, in particular a hydraulic oil system or a lubricating oil system, comprising a sensor for monitoring the impurity content of the oil in the oil system, the sensor detecting a value which is correlated with the impurity content. A particularly cost-effective construction is achieved, if the sensor is configured as a turbidity sensor which measures the turbidity of the oil, which has been caused by the impurity content.

12 Claims, 3 Drawing Sheets

OIL SYSTEM, IN PARTICULAR A HYDRAULIC OR LUBRICATING OIL SYSTEM

CROSS REFERENCE TO RELATED APPLICATIONS

Figure 1:
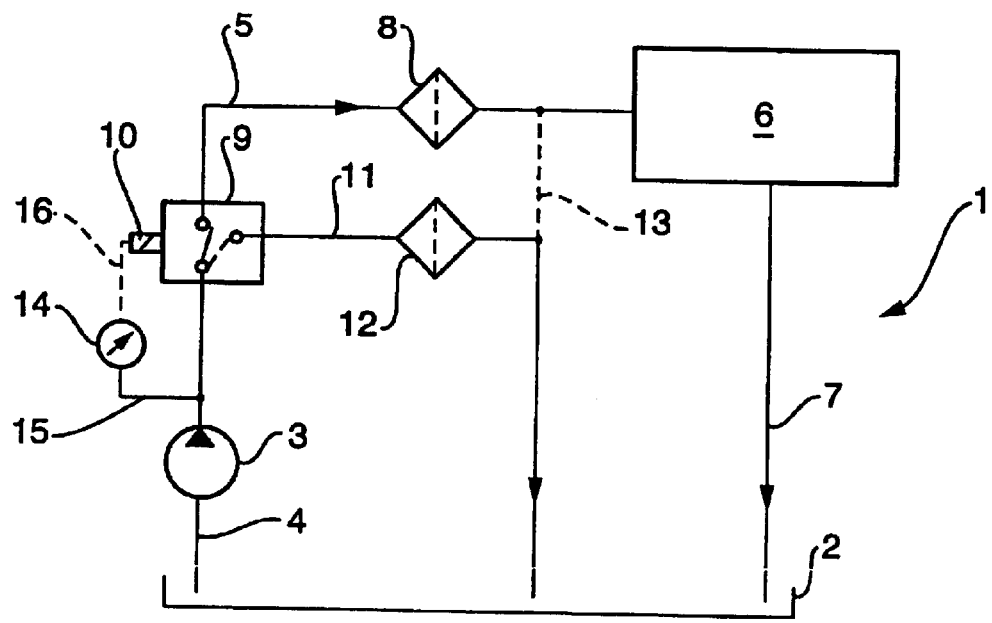

Applicants claim priority under 35 U.S.C. §119 of German Application No. 199 57 592.4 filed Nov. 30, 1999. Applicants also claim priority under 35 U.S.C. §120 of PCT/DE00/04234 filed Nov. 29, 2000. The international application under PCT article 21(2) was not published in English.

This invention relates to an oil system, in particular a hydraulic system or a lubricating oil system, having the features of the preamble of claim 1. This invention also relates to a filter for such an oil system as well as the use of a turbidity sensor in such an oil system.

Hydraulic oils and lubricating oils should be designed to be environmentally friendly, in particular biodegradable, for reasons of environmental safety. These conditions lead to oils having a comparatively low stability with respect to hydrolytic cleavage in contact with water. Therefore, in the case of oils, in particular rapidly biodegradable oils, but also traditional mineral oils, a low water content makes a considerable contribution to a long oil standing time. An unacceptably high water content can lead to aging products, especially by way of hydrolysis, and can cause material problems and function problems in the equipment supplied or working with these oils. Likewise, serious damage or functional disorders may be caused in hydraulic systems due to thermal decomposition of the oil, due to dissolution or due to chemical attack on components. Such damage can be prevented by a sensor which detects the impurity content in oil, e.g., by shutting down the oil system promptly.

British Patent 2,194,333 A describes a sensor for monitoring the impurity content in an oil. The sensor senses a value which correlates with the impurity content and is configured as a turbidity sensor which measures the turbidity of the oil which occurs as a function of the impurity content. To this end, the oil to be monitored, or at least a partial stream thereof, is passed through a measuring distance in which light is beamed into the oil to be monitored. The light transmitted by the oil in the measuring distance is measured and a signal value that correlates with the impurity content is generated as a function of the measured intensity of the transmitted light, and this signal value is used to monitor the impurity content in the oil.

U.S. Pat. No. 4,499,376 discloses a device for measuring a particle impurity in a liquid, whereby the measurements are based on the permeability of the liquid for infrared light. Accordingly, an infrared sensor measures a turbidity of the liquid which occurs as a function of the impurity content and it generates electric signals that correlate with it.

U.S. Pat. No. 5,599,460 describes a filter for an oil system which contains in a housing a filter element and a sensor for monitoring the impurity content in the oil. The sensor is situated upstream from the filter element in the housing.

In their article "Perspectives for environmentally friendly hydraulics," printed on pages 352 through 367 of the journal "o+p Ölhydraulik und Pneumatik" [Oil Hydraulics and Pneumatics], vol. 41 (1997) no. 5, on page 359, Kempermann, Remmelmann and Werner present an oil system in which a hydraulic pump connected to a reservoir on the intake side supplies oil to a feeder line on the pressure side. This feeder line carries the oil to a hydraulic system that is driven or operates with the oil. Downstream from this hydraulic system, the oil is sent back to a reservoir. Downstream from the hydraulic pump and upstream from the hydraulic system, a bypass line is connected to the feeder line; an electromagnetically switchable valve is situated in this bypass line and downstream from this valve there is a water-absorbent filter element. The bypass line also opens into a reservoir, bypassing the hydraulic system. Upstream from the hydraulic system, a sensor is arranged in the feeder line upstream from the bypass connection; this sensor monitors the water content in the oil and detects when it exceeds a saturation limit.

The sensor used for this purpose determines the increase in flow resistance of a pilot stream through a layer of water-absorbent starch polymers. If the pressure medium occurs, i.e., the hydraulic oil, becomes oversaturated, the polymer swells due to uptake of water. The elevated pressure acts on a differential pressure switch which thus delivers the desired warning signal. To this extent, this sensor senses a value which correlates with the water content of the oil.

The sensor is connected to the above-mentioned valve, which blocks the bypass in a first switch position and opens it in a second switch position. As soon as the sensor senses that the saturation limit has been reached, the sensor switches the valve, thus opening the bypass, so that the oil contaminated with an elevated water content flows through the filter element. In this way, the unwanted water content of the oil can be reduced.

In "MSR Magazine" 1-2/199, pages 10 and 11, Lauri Tuomaala reports on methods of measuring the moisture content or the water content of the oil in a lubrication system of a paper machine. By monitoring the water content of the oil in the lubrication system in combination with corresponding measures to reduce the water content of the oil, the maintenance costs of an installation equipped with this lubrication system can be greatly reduced and the useful life of the installation can be prolonged. To monitor the water content, a measuring transducer or sensor is used, measuring the water content of the oil on the basis of the water activity. The water activity correlates with the water content of the oil.

In order for a washing machine for washing clothing items to have the lowest possible water consumption for ecological reasons, modern washing machines may be equipped with a turbidity sensor which measures the degree of soiling of the wash water. As long as the degree of soiling of the wash water used for cleaning items of clothing remains below a certain threshold value, the wash water need not be replaced by fresh water. In this way, the water consumption of this washing machine depends on the degree of soiling of the laundry washed with it.

The present invention is concerned with the problem of providing expedient options for an oil system of the type defined in the preamble that will permit economical monitoring of the impurity content in oil.

This problem is solved according to this invention by an oil system having the features of claim 1.

This invention is based on the general idea of using an essentially known turbidity sensor, which operates on an optical principle, for monitoring the impurity content in oil. In doing so, this invention is making use of the finding that the impurity content in oil also causes a visually detectable turbidity which correlates with the impurity content of the oil. This finding is surprising at least inasmuch as oil, in comparison with water, is relatively impermeable for visible light. It was surprising to discover that water, whose light permeability is usually greater than that of oil, can cause turbidity in oil under the specific conditions prevailing in an oil system. Liquids, in particular water, lead to the development of finely distributed droplets in the oil or form a type of emulsion under the operating conditions of an oil system (oil pressure, flow conditions, turbulence). Optical effects in particular, such as refraction and movement of light at the media boundaries, then result in turbidity of the oil.

The term "turbidity" is understood here to refer to a reduced permeability or transmission of the oil for beams of light, in particular for infrared light. Since the light permeability of water and oil differ greatly, especially in the infrared range, an increasing water content causes a decrease in the transmission of infrared light and thus an increase in the turbidity of the oil.

Since such turbidity sensors are essentially known and are available commercially at low cost, this yields a price advantage for the oil system according to this invention. In addition, experiments have shown that the turbidity sensor operates relatively inaccurately and responds even at a relatively low impurity content or water content in the oil.

According to a preferred embodiment, the turbidity sensor may be situated upstream from a switching valve in a feeder line, the switching valve in a first switch position supplying the oil to an equipment arrangement that operates with and/or is supplied with oil through the feeder line, and in a second switch position supplying the oil into a bypass line where an element suitable for reducing the impurity content of the oil flowing through it is situated, whereby the turbidity sensor or a control unit communicating with the turbidity sensor actuates the switching valve. Due to this arrangement, the turbidity sensor can cause the switching valve to switch to the bypass line as soon as a threshold value for the impurity content is reached. On the other hand, this arrangement also makes it possible to switch the switching valve back for supplying the equipment arrangement as soon as the impurity content drops back to an allowed range again.

The problem on which the invention is based is also solved by a filter having the features of claim 8. By integration of the sensor and the element which reduces impurities into a filter housing and by arranging the sensor inside the housing upstream from a filter element, this yields an especially compact design which also guarantees that the filter element does not have a negative effect on the measurement of the impurity content in oil.

The problem on which the invention is based is also solved by a method having the features of claim 9. This method makes use of the finding that under the conditions prevailing in an oil system, light, especially infrared light, passes through the oil essentially unhindered while it is absorbed or scattered by water to varying degrees. Accordingly, the transmission of light through the oil changes as a function of the water content. By analysis of the transmission; the water content of the oil can be monitored, and through corresponding actuation of the switching valve, the water content may optionally be reduced.

The problem on which this invention is based is ultimately solved by using a turbidity sensor according to the features of claim 12. This makes use of the finding that the sensor, which is designed for detecting turbidity in water, can essentially also be used to detect an impurity content, in particular a water content, in oil under the operating conditions of an oil system, especially if the sensor operates with infrared light. Since such a turbidity sensor is known per se, monitoring of the water content of the oil of an oil system can be implemented in an especially economical manner.

Other important features and advantages of the device according to this invention are derived from the subclaims, from the drawings and from the respective description of the figures on the basis of the drawings.

Preferred embodiments of this invention are illustrated in the drawings and are explained in greater detail in the following description.

Figure 2:
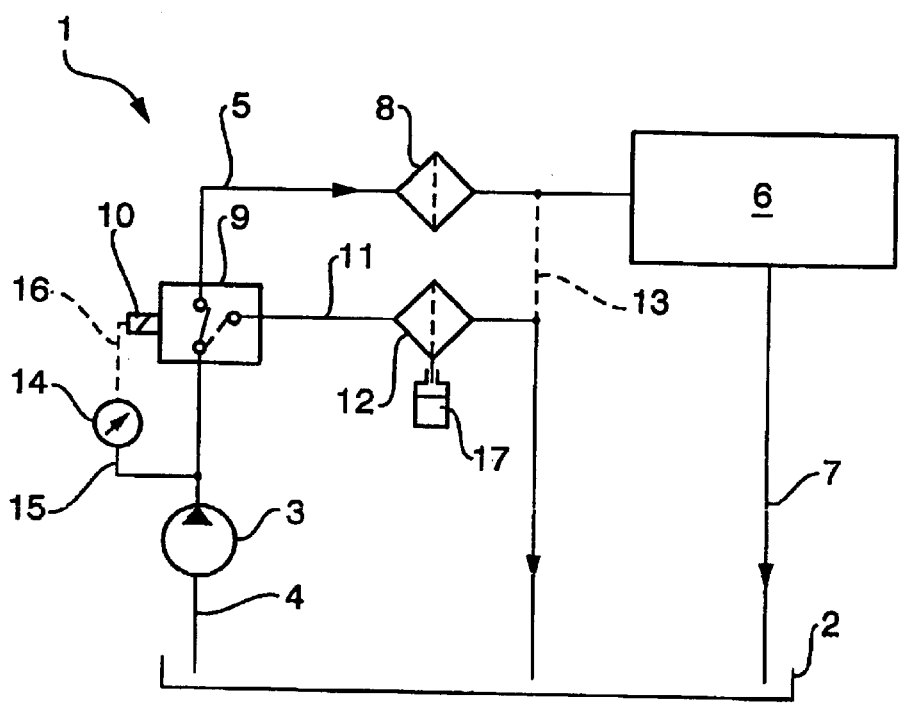
Figure 3:
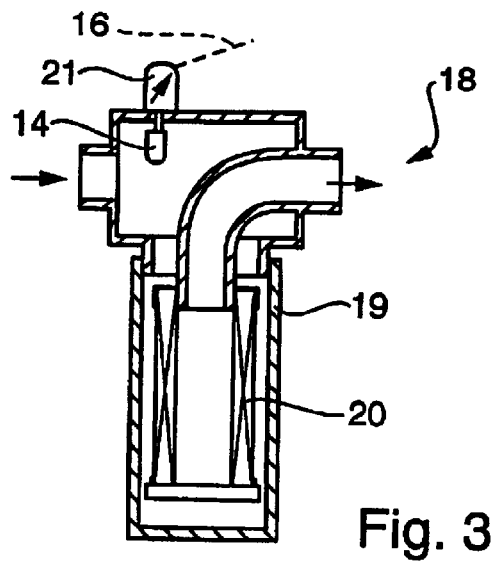
Figure 4:
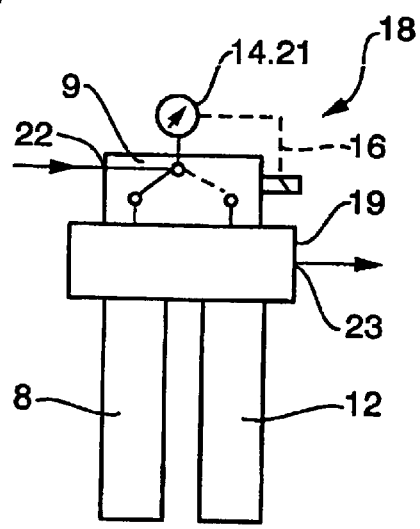
Figure 5:
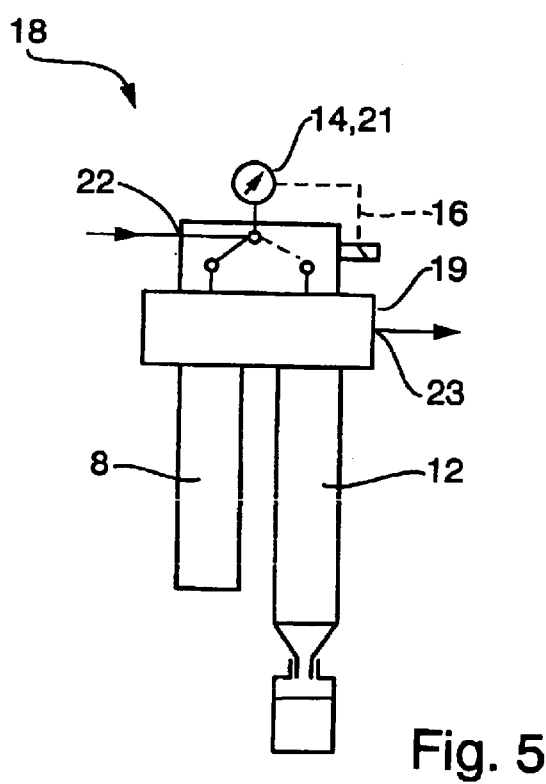
Figure 6:
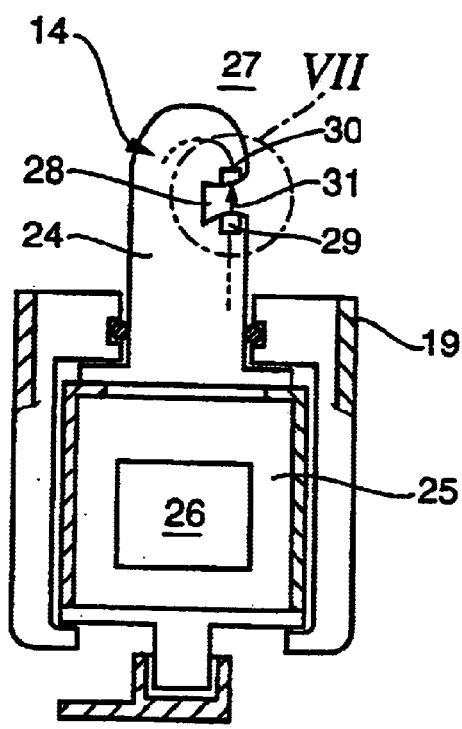

The drawings show schematically:

FIG. 1 a block diagram like a schematic of a first embodiment of an oil circuit designed according to this invention;

FIG. 2 a diagram like that in FIG. 1, but a second embodiment;

FIG. 3 a sectional view through a filter in a first embodiment designed according to this invention;

FIG. 4 a simplified block diagram of a filter according to FIG. 3, but in another embodiment;

FIG. 5 a diagram like that in FIG. 4, but in another embodiment;

FIG. 6 a block diagram of a turbidity sensor, and

Figure 7:
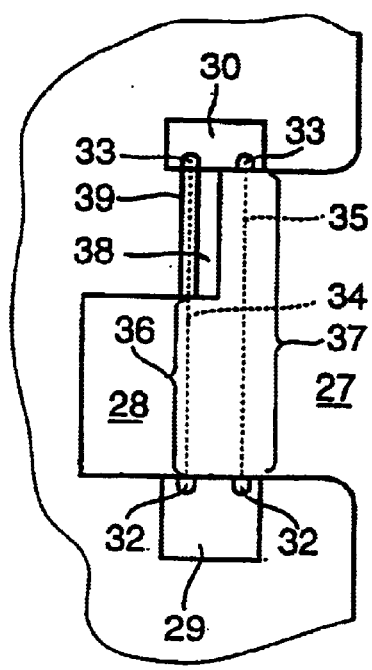

FIG. 7 a detail view according to VII in FIG. 6 in a special embodiment.

Since the use of a turbidity sensor to monitor the water content of oil in an oil system is of primary importance, the embodiments described below are always explained with respect to a turbidity in the oil due to the presence of water. However, it is self-evident that the turbidity sensor is essentially suitable for monitoring any turbidity in oil, regardless of its cause. For example, the carbon black content of the respective oil can be monitored. Examples of oils whose soiling or turbidity is to be monitored include, for example, lubricating oil, motor oil, heating oil and diesel oil. Applications in motor vehicles, e.g., to monitor the soiling of the motor oil or the fuel, whether gasoline or diesel, are also of interest. For example, the carbon black content of motor oil can be monitored in a vehicle to thereby determine the degree of soiling of an oil filter.

According to FIGS. 1 and 2, an oil system 1 according to this invention has an oil reservoir 2 from which an oil pump 3 draws oil. The oil pump 3 is connected at the intake side to the reservoir 2 by an intake line 4. At the pressure side the oil pump 3 conveys oil into a feeder line 5 which delivers oil to an equipment arrangement 6 which needs the oil. The equipment arrangement 6 may be a machine or a machine installation, for example, which is supplied with oil for lubrication. Oil system 1 then forms a lubricating oil system. Likewise, the equipment arrangement 6 may be a single hydraulic unit or a complete hydraulic system, e.g., a machine. In this case, oil system 1 forms a hydraulic oil system.

Downstream from the equipment arrangement 6, the oil is returned to the reservoir 2 through a return line 7. Upstream from the equipment arrangement 6, an oil filter 8 is provided in the feeder line 5 to filter out the conventional impurities, especially suspended particles or the like, out of the oil. A switching valve 9 which is situated between the oil filter 8 and the oil pump 3 can be switched between at least two switch positions by means of an electromagnetic control element 10. In a first switch position, the switching valve 9 connects the pressure side of the pump 3 to the section of the feeder line 5 leading to the equipment arrangement 6. In a second switch position, the switching valve 9 connects the pressure side of the pump 3 to a bypass line 11, which leads back to the reservoir 2, bypassing the oil filter 8 and the equipment arrangement 6. A water extracting element 12 is situated in this bypass line 11 to reduce the water content of the oil as the oil flows through it. Downstream from the water extracting element 12, the bypass line 11 may be connected to the feeder line 5 by a supply line 13, represented with a broken line, downstream from the oil filter 8 in a special embodiment. In this way, the equipment arrangement 6 may also be supplied with oil (from which the water has been removed) when the switching valve 9 is in its second switch position. Likewise, a mixed conveyance of the dehydrated oil downstream from the water extracting element 12 is also possible, whereby the oil is sent partially to the equipment arrangement 6 and partially to the reservoir 2; the corresponding valve means are not shown here.

Between the switching valve 9 and the oil pump 3, a sensor 14 communicates with the oil conveyed. This sensor 14 may communicate with the feeder line 5 through a corresponding connecting line 15, as shown in FIGS. 1 and 2. However, embodiments in which the sensor 14 is situated directly in the oil flow are preferred, whereby it may be integrated into the feeder line 5, for example. The sensor 14 monitors the water content of the oil and actuates the switching valve 9 over a corresponding line 16 as soon as the water content of the oil has reached a critical level. According to this invention, the sensor 14 is designed as a turbidity sensor whose functioning is described further below, specifically in conjunction with FIG. 6.

Although the arrangement of the sensor 14 upstream from the switching valve 9 as selected here is preferred, it may be quite appropriate to mount the sensor 14 at another location in the oil system 1, e.g., in the reservoir 2 or in the return line 7.

The embodiments in FIGS. 1 and 2 differ in the type of water extracting element 12. In the embodiment according to FIG. 1, the water extracting element 12 is an absorber which may be designed in the form of a filter element. The absorber stores the water extracted from the oil. A water extracting element 12 designed as an absorber contains, for example, a gel-filled filter element which forms a chemical bond with the water removed from the oil. In contrast with that, in the embodiment according to FIG. 2, the water extracting element 12 is formed by a coalescer, which separates the water from the oil as the oil laden with water flows through it, and allows the water to flow out of the oil flow. The water removed in this way may be collected in a separate container 17. Since both absorbers and coalescers are known in general, a more extensive description of these components may be omitted.

The oil system 1 presented in the embodiments in FIGS. 1 and 2 functions as follows:

In normal operation, the oil contains an allowed amount of impurities, in particular water, so that the turbidity sensor 14 or a controller connected to it switches the switching valve 9 into its first switch position. Accordingly the oil flows through the oil filter 8 to the equipment arrangement 6. Since the bypass line 11 does not have flow through it in normal operation, no flow can develop through the water extracting element 12, so that it is protected in normal operation and is ready for use for emergency operation.

As soon as the turbidity sensor 14 detects an inadmissibly high impurity content or water content in the oil, the switching valve 9 is switched into its second switch position, thereby activating emergency operation. The oil, which is loaded with water, is then sent to bypass 11 and flows through the water extracting element 12. This emergency operation is maintained until the turbidity sensor 14 again senses an admissible impurity content or water content and switches back to normal operation or the switching valve 9 switches to its first switch position.

Since a traditional oil filter may also have the property of extracting water from the oil, the oil filter 8 may become rapidly saturated when the water content is inadmissibly high. This can be avoided because the bypass 11 bypasses the oil filter 8.

According to FIGS. 3, 4 and 5, a filter 18 according to this invention has a housing 19 in which is arranged a filter element 20. The filter element may be an oil filter element, so that this filter 18 forms an oil filter, which corresponds to the oil filter 8 of the oil system 1 shown in FIGS. 1 and 2, for example. Likewise, the filter element 20 may be an absorber filter element.

In the housing 19 of the filter 18, the turbidity sensor 14 is situated upstream from the filter element 20. An analyzer unit or a controller 21 of the turbidity sensor 14 is then connected to the switching valve 9 over the line 16.

According to a preferred embodiment illustrated in FIG. 4, switching valve 9 may be integrated into the housing 19 of the filter 18. In addition, both the oil filter 8 and the water extracting element 12 are designed in the housing 19, with separate flow paths being designed in the interior of the housing 19 accordingly. In normal operation, the switching valve 9 switches an inlet 22 of the filter 18 to the oil filter 8, and in emergency operation, it switches to the water extracting element 12. With the embodiments illustrated in FIG. 5, the filter housing 19 has only one outlet 23; likewise, an embodiment with two outputs may be provided.

The embodiments of FIGS. 4 and 5 differ essentially in the type of water extracting element 12, which is preferably formed by an absorber in the variant according to FIG. 4 and by a coalescer in the variant according to FIG. 5.

According to FIG. 6, a turbidity sensor 14 according to this invention has a bolt-like sensor section 24 and a control unit 25, which may contain electronics 26 as well as a controller, an analyzer unit and the like. The sensor 14 is mounted so that its sensor section 24 projects into a space 27 through which the oil to be monitored flows, the control unit 25 may be situated outside the space 27. Accordingly, the sensor section 24 penetrates through the housing 19, for example.

The sensor 14 has in its sensor section 24 a measuring distance 28 which is open toward the space 27 and accordingly is penetrated by the oil in space 27 or through which the oil may flow. In addition, there is at least one sensor 29 which beams light, preferably infrared light, into the measuring distance 28 and thus into the oil in it. The infrared light passes through the measuring distance 28 and in general strikes at least one receiver 30, which senses the incoming light intensity. The transmission of the infrared light through the measuring distance 28 and through the oil in it is represented symbolically by an arrow 31 in FIG. 6.

Transmitter 29 and receiver 30 are connected to the control unit 25, in which an analyzer unit, for example, may generate a signal value that correlates with the transmission 31. Since certain wavelengths of light are preferred for the beam of light, in particular in the infrared range, the beam of light may pass almost unhindered through oil which does not have any turbidity, whereas the beam of light is increasingly hindered with an increase in water content, i.e., with increasing turbidity. In other words, the greater the water content of the oil, the less light can be sensed by the receiver 30. The reduction in the infrared light transmission with an increase in the water content is the result of an absorption effect of the water with respect to infrared light on the one hand, while on the other hand, the water in the oil system regularly occurs as an emulsion in the oil, so that diffraction, refraction and dispersion effects can also interfere with the transmission.

Experiments have shown that in operation with light at a wavelength of 750 nm to 1000 nm, preferably 880 nm, the sensor 14 has an especially high sensitivity with regard to water present in the oil, so that a relatively low water content can be detected in the oil.

FIG. 7 shows a detail of the sensor 14, designated as VII in FIG. 6, on an enlarged scale, but in a preferred embodiment. The sensor 14 here has a transmitter unit 29 which has two transmission sites 32. These transmission sites 32 may be formed by two apertures, for example, which are acted upon by a common transmitter. Likewise, a separate transmitter may also be provided for each transmission site 32. In addition, the sensor 14 has a receiver unit 30, which has two receiver sites 33. Here again, the receiver sites 33 may be formed by apertures which share a common receiver. As an alternative, the receiver sites 33 may each be provided with a separate receiver.

The measuring distance 28 formed between the transmitter unit 29 and the receiver unit 30 communicates with the space 27 so that the measuring distance 28 may receive the oil to be monitored. In addition, two separate signal paths or light paths 34 and 35 are provided between the transmitter unit 29 and the receiver unit 30, symbolized here by dotted lines. The two signal paths 34, 35 differ from one another with regard to the length of their segments 36 and 37 with which they run inside the measuring distance 28, i.e., through the oil to be monitored. In the present case, the two signal paths 34 and 35 run at least partially inside of the measuring distance 28. Likewise, an embodiment in which the one signal path 34 runs completely outside the measuring distance 28 is also possible. The different lengths of their segments 36 and 37 are achieved here by a step 38 which projects into the measuring distance 28. A light-permeable line 39 is formed in this step 38, e.g., in the form of a borehole or an optical fiber.

With the help of this arrangement, the degree of soiling may be determined from a comparison of the received signals sensed at the reception sites 33. Therefore, the measurement is independent of fluctuations in current or voltage or aging phenomena in the transmitter unit 29 or in the receiver unit 30, because they act in the same way with both signal paths 34, 35. In addition, this arrangement may also be used to monitor proper functioning of the sensor 14. Due to the different lengths of the segments 36 and 37, the received signals that can be sensed in the case of turbidity are necessarily different with the two signal paths 34, 35. With increasing turbidity, the two received signals drop to different extents according to a first functional relationship. When the transmission power of the transmitter unit 29 drops because of a fluctuation in current, for example, this results in both received signals decreasing according to a second functional correlation. This difference can be recognized by a corresponding analyzer device.

What is claimed is:

1. An oil system, in particular a hydraulic system or a lubricating oil system, having a sensor (14) for monitoring the impurity content in the oil in the oil system (1), which senses a value that correlates with the impurity content, whereby the sensor is designed as a turbidity sensor (14) which measures the turbidity of the oil which occurs as a function of the impurity content, whereby the turbidity sensor (14) is situated in a feeder line (5) upstream from an equipment arrangement (6) which is supplied with and/or works with oil, characterized in that the turbidity sensor (14) is arranged upstream from a switching valve (9) in the feeder line (5), whereby the switching valve (9) in a first switch position supplies the oil to the equipment arrangement (6), and in a second switch position it supplies oil to a bypass line (11) in which is arranged an element (12) suitable for reducing the impurity content in the oil flowing through the element, whereby the turbidity sensor (14) or a controller (21) which communicates with the turbidity sensor (14) actuates the switching valve (9).

2. The oil system according to claim 1, characterized in that the turbidity sensor (14) generates a signal value which correlates with the turbidity which occurs due to the impurity content in the oil.

3. The oil system according to claim 1, characterized in that the turbidity sensor (14) is arranged in the feeder line (5) upstream from a filter element (8).

4. The oil system according to claim 1, characterized in that the element (12) suitable for reducing the impurity content is formed by an absorber or by a coalescer which reduces the liquid impurities content in the oil.

5. The oil system according to claim 1, characterized in that the bypass line (11) in a reservoir (2) and/or downstream from the filter element (8) and upstream from the equipment arrangement (6) opens into the feeder line (5).

6. The oil system according to claim 1, characterized in that the turbidity sensor (14) has at least one transmitter (29) and at least one receiver (30), between which is formed a measuring distance (28), which receives the oil to be monitored, and two separate signal paths (34, 35), whereby at least one of the signal paths (34, 35) runs inside the measuring distance (28), and whereby the two signal paths (34, 35) differ from one another with regard to the length of their segments (36, 37) within the measuring distance (28).

7. The oil system according to claim 6, characterized in that to determine the signal value which correlates with the turbidity and/or to monitor for proper functioning of the turbidity sensor (14), the received signal received over the one signal path (34) is compared with the received signal received over the other signal path (35).

8. A filter for an oil system, in particular according to claim 1, whereby the oil system (1) has a sensor (14) for monitoring the impurity content in the oil of the oil system (1), which senses a value that correlates with the impurity content, whereby the filter (18) has a housing (19) in which a filter element (8) is arranged for purifying the oil, whereby the sensor (14) is situated in the housing (19) upstream from the filter element (8) characterized in that an element (12) for reducing the impurity content in the oil is also arranged in the housing (19), whereby in addition, a switching valve (9) is also arranged in the housing (19), 50 that in a first switch position it connects an inlet (22) of the housing (19) to the oil filter element (8), and in a second switch position it connects the inlet (22) to the reducing element (12).

9. A method of monitoring the impurity content in the oil of an oil system according to claim 1, whereby the oil to be monitored or at least a partial stream thereof is sent through a measuring distance (28); light is beamed into the oil to be monitored in the measuring distance (28); the light transmitted by the oil in the measuring distance (28) is measured; a signal value that correlates with the impurity content in the oil is generated as a function of the measured intensity of the transmitted light and is used to monitor the impurity content in the oil characterized in that for normal operation in which the oil has an admissible impurities content, the switching valve (9) is switched to the first switch position, in which the oil flows through an oil filter (8) to the equipment arrangement (6), whereby for emergency operation in which the oil has an inadmissibly high impurities content, the switching valve (9) is switched to the second switch position in which the oil flows through the bypass line (11) and the reducing element (12).

10. The method according to claim 9, characterized in that the light used is infrared light which has a wavelength of 750 nm to 1000 nm, preferably 880 nm.

11. The method according to claim 9, characterized in that to determine the signal value that correlates with the turbidity and/or to monitor for proper functioning of the turbidity sensor (14), a first measured intensity is compared with a second measured intensity, whereby the two intensities are assigned to different light paths (34, 35) which differ with regard to the length of their segments (36, 37) within the measuring distance (28).

12. A use of a turbidity sensor (14) having a measuring distance (28) which is suitable for through-flow with a liquid to be monitored, having at least one transmitter (29) which beams light into the measuring distance (28) in the liquid, having at least one receiver (30) which measures the intensity of the light which is transmitted through the liquid in the measuring, distance (28) for carrying out the method according to claim 9.

* * * * *